United States Patent [19]

Ramkissoon

[11] Patent Number: 5,240,653
[45] Date of Patent: Aug. 31, 1993

[54] HOUSE FRESHENER

[76] Inventor: Kaywal K. Ramkissoon, 15332 Aylesbury St., Silver Spring, Md. 20905

[21] Appl. No.: 760,711

[22] Filed: Sep. 16, 1991

[51] Int. Cl.⁵ .................................. A61L 9/12
[52] U.S. Cl. ................... 261/99; 55/279; 239/56; 261/107; 261/DIG. 17; 261/DIG. 65; 422/123; 428/905; D23/366
[58] Field of Search .............. 261/30, 99, 104, 107, 261/DIG. 15, DIG. 17, DIG. 41, DIG. 65; 55/279; 239/60, 53-57; 454/328, 337; 422/123, 124; 428/905; D23/366; 224/30 R, 36, 30 A; 248/206.5, 309.4; 269/8

[56] References Cited

U.S. PATENT DOCUMENTS

| | | | |
|---|---|---|---|
| 3,442,197 | 5/1969 | Cobarg | D23/366 X |
| 4,118,226 | 10/1978 | Bourassa | 55/279 |
| 4,159,672 | 7/1979 | Garguilo et al. | 261/104 X |
| 4,229,415 | 10/1980 | Bryson | 261/DIG. 17 |
| 4,306,892 | 12/1981 | Atalla et al. | 55/279 |
| 4,428,892 | 1/1984 | Berliner | 261/99 |
| 4,563,333 | 1/1986 | Frigon | 55/279 X |
| 4,604,114 | 8/1986 | Ward | 55/279 |
| 4,676,954 | 6/1987 | Wilson | 261/104 X |
| 4,875,912 | 10/1989 | Fulmer | 55/279 |

FOREIGN PATENT DOCUMENTS 2411011 8/1979 France .................. 261/104

*Primary Examiner*—Richard L. Chiesa
*Attorney, Agent, or Firm*—S. Michael Bender

[57] ABSTRACT

A basket fitting is provided for an air filter used in the air circulation ducting of a domestic dwelling and is designed to be attached directly to the duct covering grill within a room. Various air fresheners and germicidal agents may be retained within a particular basket attached to a grill, as can a charcoal filtering agent, and in one preferred embodiment, a plurality of these baskets may be interconnected to enhance the effectiveness of the invention.

1 Claim, 5 Drawing Sheets

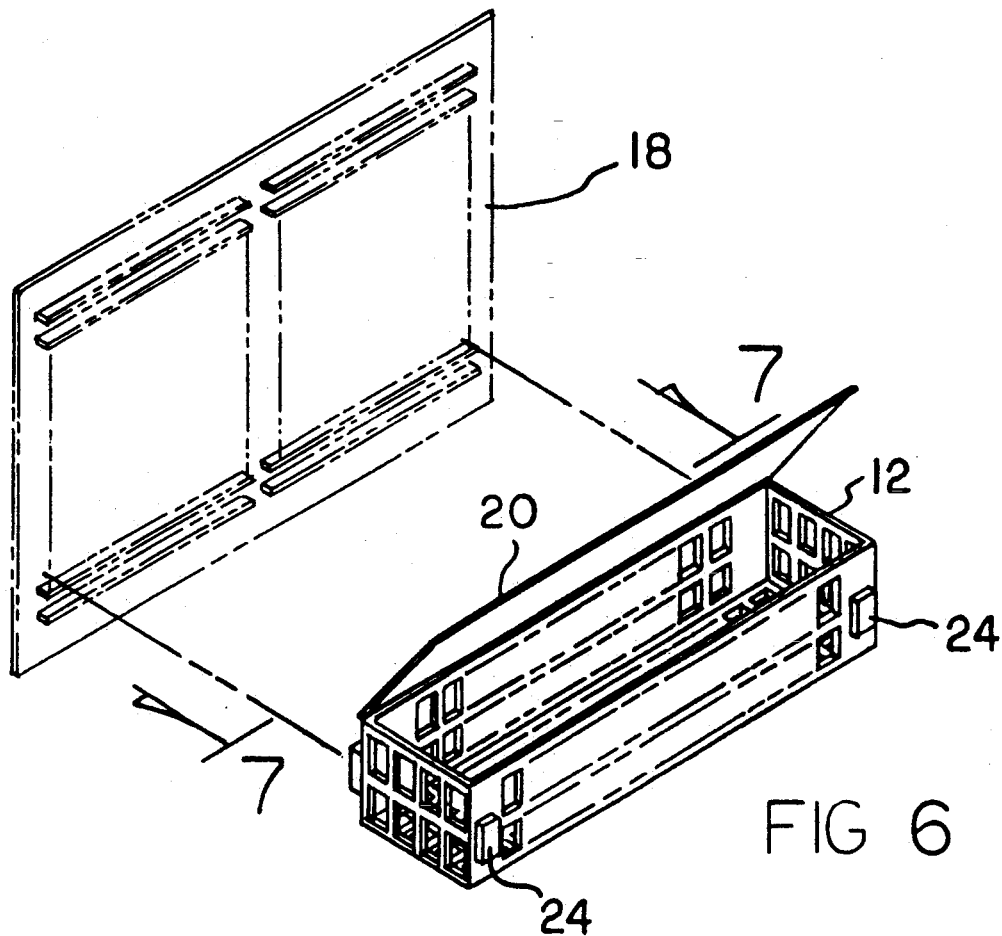
FIG 6
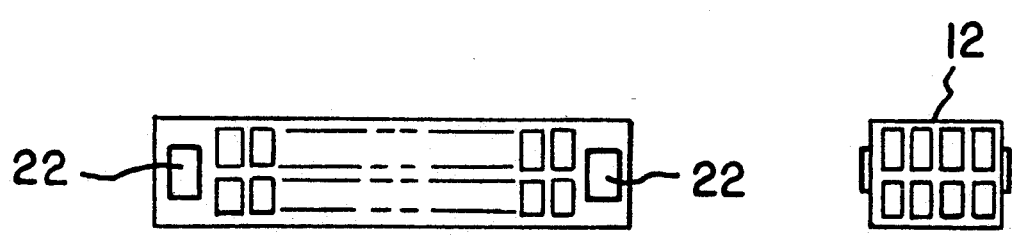
FIG 7
FIG 8

HOUSE FRESHENER

BACKGROUND OF THE INVENTION

1. Field of the Invention

The present invention relates to deodorizing systems for dwelling interiors, and more particularly pertains to a deodorizer and air freshener holder which is attachable to the front portion of an air circulation duct grill.

2. Description of the Prior Art

The use of air fresheners and deodorizing fittings in combination with air circulating duct work is known in the prior art. In this respect, various means have been patented for accomplishing an air freshening function through the use of an existing air circulating duct work. For example, U.S. Pat. No. 4,118,226, which issued to R. Bourassa on Oct. 3, 1978, discloses a combination air filter and air treating device for use in a forced air type ventilation heating and cooling system wherein the air freshener or germicidal element associated therewith is made an integral part of a filter element casing. The entire assembly is disposable, including the filter, after the air freshener or germicidal material has been totally used.

U.S Pat. No. 4,306,892, which issued to Atalla et al. on Dec. 22, 1981, discloses a disposable air freshening packet which contains an air freshening medium and is formed with securing elements to facilitate its positioning within an air stream associated with an existing air circulation system. This packet provides no filtering function but rather is designed to allow the slow evaporation of the air freshening medium as air is forced through the packet.

Another invention of interest is to be found in U.S. Pat. No. 4,563,333 which issued to W. Frigon on Jan. 7, 1986. This patent discloses a deodorizing fitting which is attachable to an air filter used in the air circulation ducting of a domestic dwelling or other building and operates to deodorize the circulating air. The fitting effectively comprises a rectangular envelope of perforated cardboard with a deodorizing insert therein, while adhesively-backed tabs on adjacent edges of the envelope facilitate its attachment to an existing air filter.

U.S. Pat. No. 4,604,114, which issued to R. Ward on Aug. 5, 1986, discloses a fragrant scented air filter particularly adapted for use in conjunction with interior building air conditioning systems. As was above discussed with reference to U.S. Pat. No. 4,118,226, this patent also relates to a disposable filter having an air freshening medium contained therein.

Of more recent interest is U.S. Pat. No. 4,875,912, which issued to T. Fulmer on Oct. 24, 1989, wherein a scented furnace filter is described. A scented evaporant packet is inserted in a cut out portion of an existing air filter, and the evaporant is then exposed to the air flowing in the cold air duct of the furnace.

While all of the above-described inventions are functional for their intended purposes, it can be appreciated that each of these devices is intended to be attached directly to or form a part of an existing furnace filter. Quite frequently, furnace filters are hard to access and further, any scent attached directly to a filter will be dispensed throughout every room of a dwelling. It can be appreciated that there might be situations where it would be desirable to have a scent directed only to a particular room and further, it would be useful to attach such scent holding devices directly to the external grill work located at the end of each section of ducting directed to a particular room, thereby making it much easier to attach and remove the scent holders. The present invention substantially addresses these needs and solves the associated problems.

SUMMARY OF THE INVENTION

In view of the foregoing disadvantages inherent in the known types of air freshening fittings now present in the prior art, the present invention provides an improved air freshening fitting construction wherein the same can be directly attached to ducting grills. As such, the general purpose of the present invention, which will be described subsequently in greater detail, is to provide a new and improved air freshening fitting which has all the advantages of the prior art air freshening fittings and none of the disadvantages.

To attain this, the present invention essentially comprises a basket fitting which is provided for an air filter used in the air circulation ducting of a domestic dwelling and is designed to be attached directly to the duct covering grill work within a room. Various air fresheners and germicidal agents may be retained within a particular basket attached to a grill, as can a charcoal filtering agent, and in one preferred embodiment, a plurality of these baskets may be interconnected to enhance the effectiveness of the invention.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved air freshening fitting which has all the advantages of the prior art air freshening fittings and none of the disadvantages.

It is another object of the present invention to provide a new and improved air freshening fitting which may be easily and efficiently manufactured and marketed.

It is a further object of the present invention to provide a new and improved air freshening fitting which is of a durable and reliable construction.

An even further object of the present invention is to provide a new and improved air freshening fitting which is susceptible of a low cost of manufacture with regard to both materials and labor, and which accordingly is then susceptible of low prices of sale to the consuming public, thereby making such air freshening fittings economically available to the buying public.

Still yet another object of the present invention is to provide a new and improved air freshening fitting which provides in the apparatuses and methods of the prior art some of the advantages thereof, while simultaneously overcoming some of the disadvantages normally associated therewith.

Still another object of the present invention is to provide a new and improved air freshening fitting which may be attached directly to ducting covers, thereby eliminating the need for accessing a furnace filter to achieve the same result.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a perspective view of a second embodiment of the invention.

FIG. 7 is a rear elevation view of the second embodiment of the invention as viewed along the line 7—7 in FIG. 6.

FIG. 8 is an end elevation view of the second embodiment of the invention.

DESCRIPTION OF THE PREFERRED EMBODIMENTS

Figure 1:
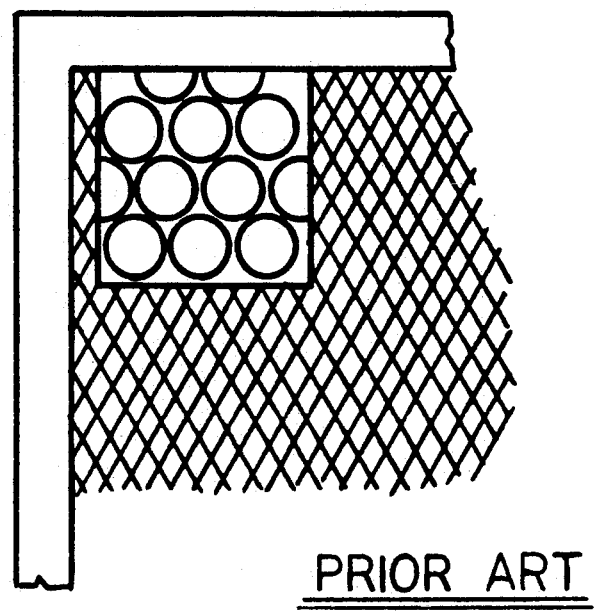
FIG. 1 is a partial front elevation view of a prior art scented furnace filter.

With reference now to the drawings, a new and improved air freshening fitting embodying the principles and concepts of the present invention and generally designated by the reference numeral 10 will be described.

Figure 2:
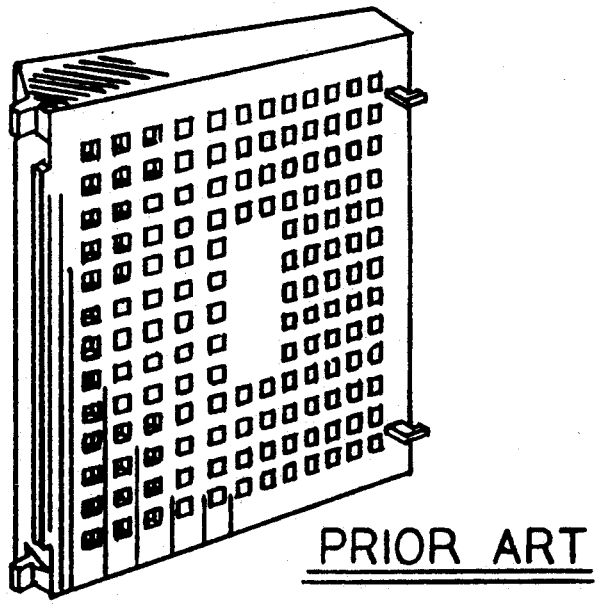
FIG. 2 is a perspective view of a prior art disposable air freshening packet.

Initially however, reference is made to FIGS. 1 and 2 of the drawings wherein best examples of existing prior art air freshening fittings are illustrated. FIG. 1 illustrates a scented furnace filter as aforediscussed with reference to U.S. Pat. No. 4,875,912, and FIG. 2 illustrates a disposable air freshening packet as aforediscussed with reference to U.S. Pat. No. 4,306,892. Both of these air freshening packets are designed to be attached to an existing furnace air filter and teach the concept of manufacturing air freshening packets and/or fittings separately from an air filter. However, neither of these packets perform the function of the present invention as will be subsequently discussed.

Figure 3:
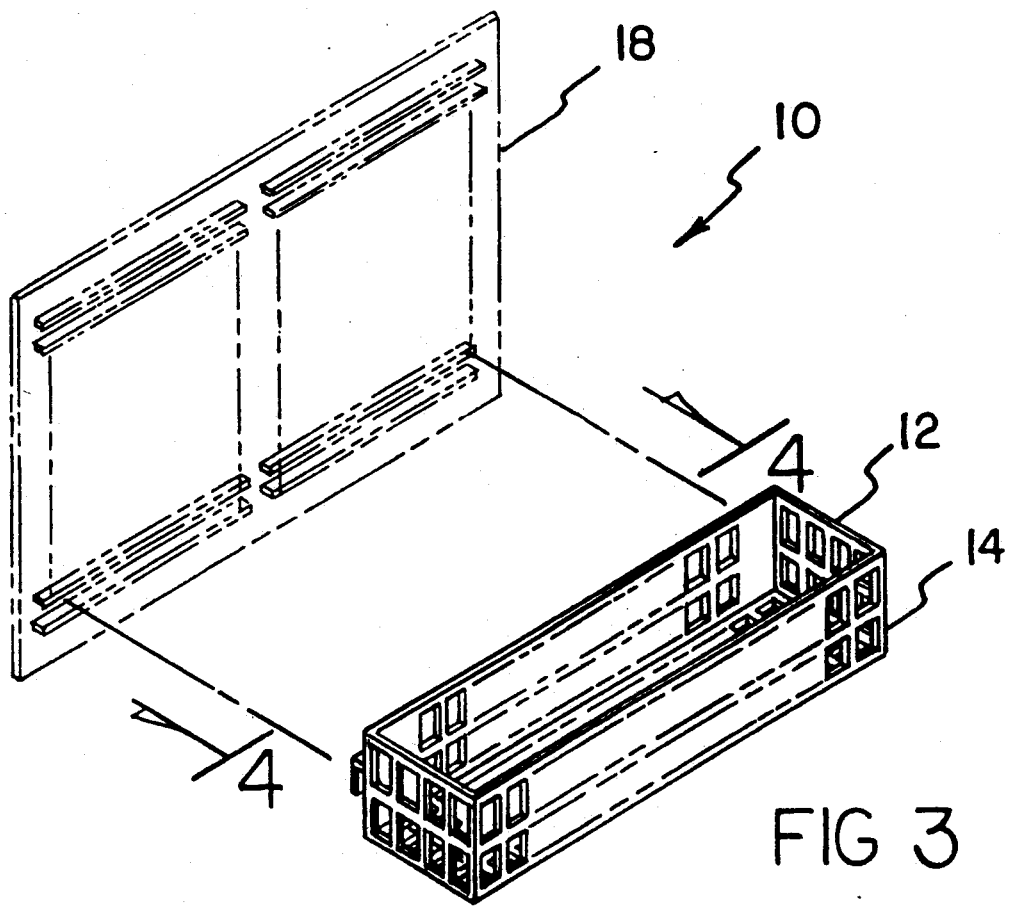
FIG. 3 is a perspective view of a first embodiment of the present invention.
Figures 4, 5:
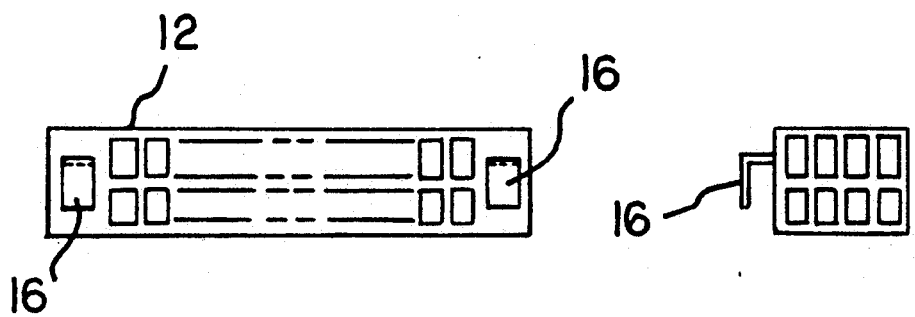
FIG. 4 is a rear elevational view of the invention as viewed along the line 4—4 in FIG. 3.
FIG. 5 is an end elevational view of the first embodiment of the invention.

FIGS. 3, 4 and 5 illustrate a first embodiment of the invention 10 wherein it can be seen that the same essentially comprises a rectangularly-shaped basket 12 having a plurality of rectangularly-shaped openings 14 positioned on all planar surfaces. This plurality of rectangular openings 14 facilitate air flow in all directions through the basket 12 when an air freshening medium is retained therein. A pair of clips 16 are integrally attached to a rear portion of the basket 12, and these clips facilitate a quick and easy removable attachment of the basket to an existing duct grill cover 18 as best shown in FIG. 3.

Figure 9:
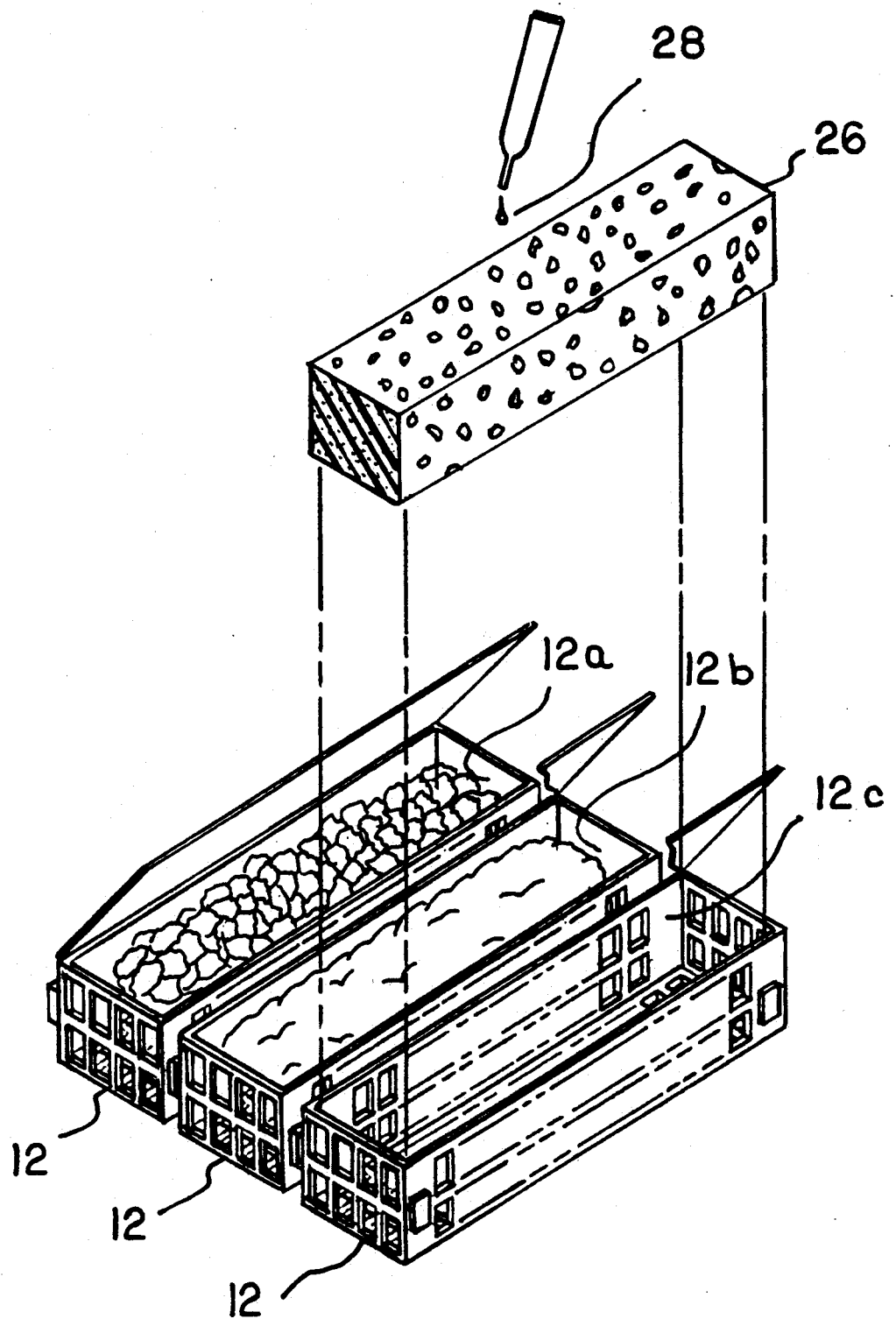
FIG. 9 is a perspective view illustrating a use of the second embodiment of the invention.

A modified embodiment of the invention is illustrated in FIGS. 6, 7 and 8 wherein the basket 12 is illustrated as having an optional pivotally attached cover 20. A first pair of magnets 22 are attached to a rear surface of the basket 12, and these magnets facilitate a magnetic attachment of the basket directly to a grill cover 18. The second pair of magnets 24 are attached to a front wall portion of the basket 12 to facilitate the interconnection of a plurality of these baskets as best illustrated in FIG. 9. More specifically, three baskets 12 are shown magnetically attached to each other in FIG. 9 and recognizing that these baskets would be made of an extremely light weight material, it has been found that several baskets can be held together along with their air freshening mediums without the necessity of providing further supporting structure when the entire assembly is attached to a grill cover 18. When several baskets 12 are interconnected, different air freshening mediums can be positioned in each of the baskets to obtain varying air freshening effects. For example, flower petals and other fragrance emitting leaves and the like could be positioned in compartment 12a associated with a first basket, and granulated charcoal powder could be positioned in compartment 12b associated with the second basket. The charcoal powder would operate to partially remove pollutants traveling within the moving air stream. A sponge 26 could be retained within compartment 12c associated with a third basket 12, and a liquid germicidal agent and/or deodorizer 28 could be used to saturate the sponge, thereby to facilitate an evaporation thereof as the moving air stream passes around the sponge.

Figure 10:
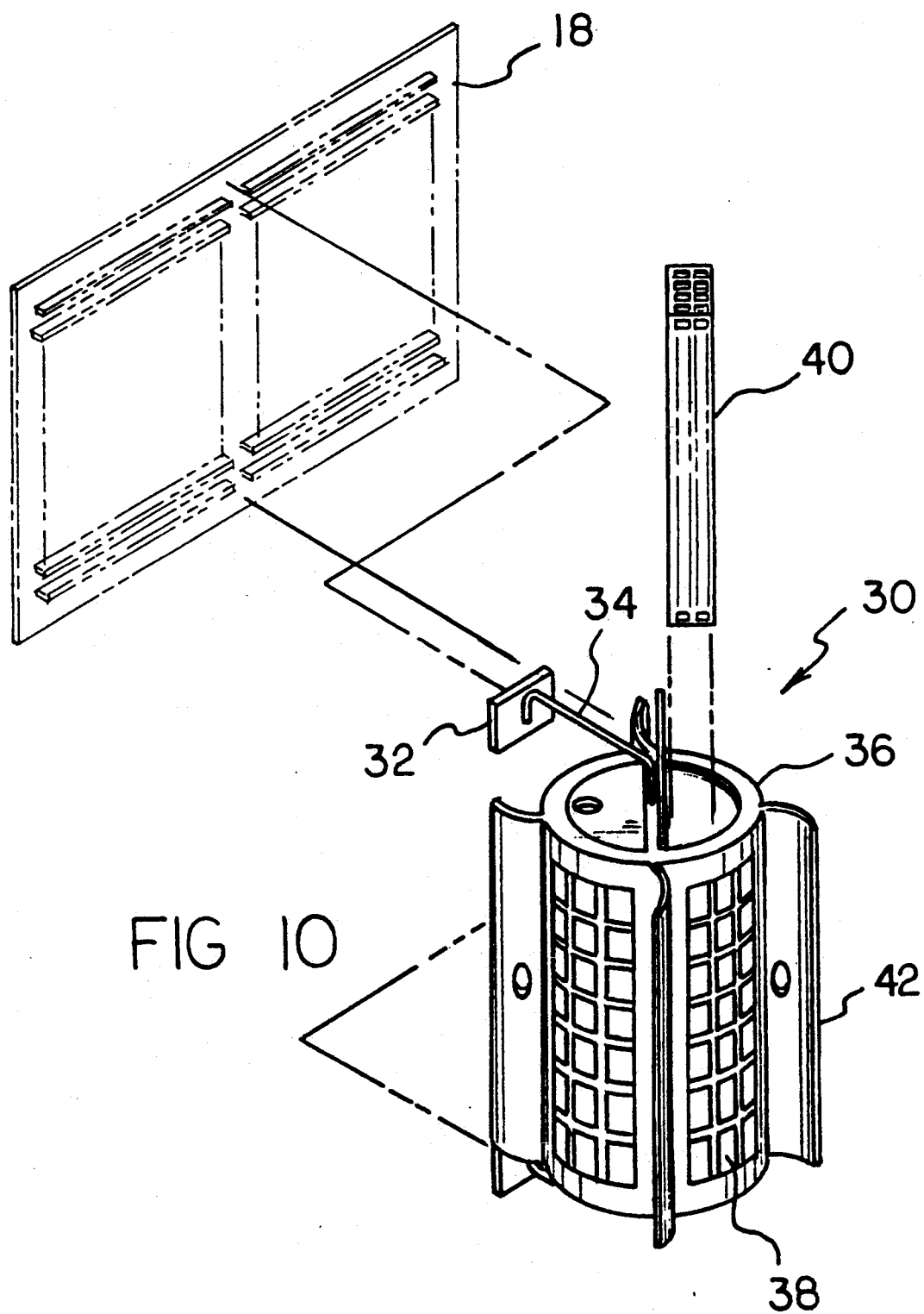
FIG. 10 is a perspective view of a third embodiment of the invention.

FIG. 10 of the drawings illustrates a final embodiment of the invention which is generally designated by the reference numeral 30. A pair of magnets 32 (only one of which is illustrated) can have respective supporting rods 34 extending outwardly therefrom, and a rotatable basket 36 could be rotatably mounted to the supporting rods. In this regard, the basket 36 is of a cylindrical construction and is provided with a plurality of rectangular apertures 38 to facilitate air flow therethrough. One or more removable baskets 40 may be positioned within an interior portion of the rotatable basket 36, and these baskets 40 may be filled with any of the aforementioned air freshening mediums as desired. Integrally attached to the basket 36 is a plurality of air foils 42 which, when positioned within the air stream of a grill cover 18, effect the continual rotation of the basket in a now apparent manner. The additional rotation of the basket 36 in combination with the movement of the air stream passing through the grill cover 18 effects a much more even distribution of the air freshening medium, as well as increasing the rate of evaporation and distribution.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved air freshening fitting for use in an existing air circulation system, said air freshening fitting having means for attaching said fitting directly to an air circulation ducting grill cover, said fitting comprising:

air freshening medium holding means
and
support means for attaching said air freshening medium holding means to said ducting grill cover;
wherein said support means comprises at least one magnet,
wherein said air freshening holding means comprises at least first and second perforated baskets, each of said at least first and second perforated baskets having a back wall and a front wall spaced from said back wall along an axis substantially perpendicular to said grill cover wherein said back wall of said first basket having means for connecting said back wall to said grill cover and said back wall of said second basket having means for connecting said back wall of said second basket to said front wall of said first basket, each of said first and second perforated baskets having means for holding an air freshening medium therein, and
magnetic attachment means for connecting said first and second perforated baskets, and wherein said at lest first and second perforated baskets having means for connecting said baskets to each other and to said grill cover in a longitudinal array along said axis.

* * * * *